(12) United States Patent
Candelore et al.

(10) Patent No.: US 11,917,368 B2
(45) Date of Patent: Feb. 27, 2024

(54) HEARING AIDS PROVIDING PROTECTION AGAINST SUDDEN LOUD SOUNDS

(71) Applicant: Sony Group Corporation, Tokyo (JP)

(72) Inventors: Brant Candelore, Poway, CA (US); Mahyar Nejat, La Jolla, CA (US)

(73) Assignee: SONY GROUP CORPORATION, Tokyo (JP)

( * ) Notice: Subject to any disclaimer, the term of this patent is extended or adjusted under 35 U.S.C. 154(b) by 0 days.

(21) Appl. No.: 17/693,152

(22) Filed: Mar. 11, 2022

(65) Prior Publication Data
US 2023/0292059 A1 Sep. 14, 2023

(51) Int. Cl.
H04R 25/00 (2006.01)

(52) U.S. Cl.
CPC ......... *H04R 25/356* (2013.01); *H04R 25/353* (2013.01)

(58) Field of Classification Search
None
See application file for complete search history.

(56) References Cited

U.S. PATENT DOCUMENTS

| | | | |
|---|---|---|---|
| 2012/0082335 A1 | 4/2012 | Duisters | |
| 2018/0005622 A1 | 1/2018 | Kyllönen | |
| 2020/0336823 A1* | 10/2020 | Volmer | .............. A42B 3/30 |
| 2020/0396552 A1* | 12/2020 | Dickinson | .............. H04R 25/604 |
| 2022/0240031 A1* | 7/2022 | Naumann | .............. H04R 25/603 |

FOREIGN PATENT DOCUMENTS

| | | |
|---|---|---|
| CN | 213368146 | 6/2021 |
| WO | WO-2020132347 A1 | 6/2020 |
| WO | WO-2022020122 A1 | 1/2022 |

OTHER PUBLICATIONS

Noise-cancelling & noise suppressing hearing protection—https://www.protectear.com/us/blog/2016/07/26/noise-cancelling-hearing-protection/—Published Jul. 26, 2016.

* cited by examiner

*Primary Examiner* — Kenny H Truong
(74) *Attorney, Agent, or Firm* — Trellis IP Law Group, PC

(57) ABSTRACT

A hearing aid includes a microphone, and a processing unit. The microphone is configured to receive sound incident on the hearing aid and deliver a corresponding microphone output to the processing unit. The processing unit is configured to process the microphone output to determine whether the incident sound comprises potentially harmful sound, and to generate a processor output including a processed version of the microphone output.

A method of protecting a hearing aid wearer from sudden loud sounds uses a microphone in the hearing aid to receive incident sound and deliver a corresponding microphone output to a processing unit in the hearing aid. The processing unit processes the microphone output to generate a first processor output, determined by whether the incident sound includes potentially harmful impulsive sound, and a second processor output including a processed version of the microphone output.

19 Claims, 4 Drawing Sheets

HEARING AIDS PROVIDING PROTECTION AGAINST SUDDEN LOUD SOUNDS

BACKGROUND

Loud sounds can be very damaging to one's hearing. People occasionally or routinely exposed to such sounds, occupationally for example, may protect themselves by wearing sound reducing or sound blocking ear plugs or headphones, but this protection generally also blocks other lower-volume sounds (like normal speech, or a ringing phone) that the wearer would ideally like to hear. In some situations, the loss of these "safe" sounds is worth accepting to avoid the risk of serious, even irreversible damage caused by the loud sounds. In many situations, however, especially when loud noises occur quite infrequently, people often risk damage by only choosing to use the protection after a sound reaches an uncomfortably loud level, rather than as a precautionary measure. This is particularly problematic if the loud sound is impulsive, meaning sound of short duration, usually less than one second. with an abrupt onset, rapid rise and, in most cases, rapid decay. Such sound may rise so suddenly that those exposed to it don't have time to take appropriate action before it reaches a dangerously high value.

Hereafter, throughout this disclosure, the term "impulsive" is defined to mean noise of duration less than one second, rising from a safe level to approach (or exceed) a potentially harmful level within 0.5 s. The terms "safe" and "harmful" should be understood to encompass a combination of loudness and duration. For example, noise at a loudness of "A" dBA persisting for "X' seconds may be considered safe, while noise at the same loudness "A" dBA persisting for "3X" seconds may be considered potentially harmful.

Now consider the particular circumstances affecting a hearing-impaired person who wears a hearing aid to amplify received sound waves from an initial volume that would be difficult to hear for that person, to levels that are audible to them. An incident sound whose loudness might be just about acceptable for people who are not hearing-impaired, and therefore receiving the sound "naturally" might well be problematic for the hearing-impaired person who receives an amplified version of that sound, delivered via the hearing aid into the ear canal. Fortunately, hearing aids have limits on the loudness of sound that will be amplified. However, sound can directly enter the ear through certain open vents in the earpiece of the aid or can be conducted through the body of the earpiece and enter the hearing canal.

Since the sound is environmental, it does not matter if the wearer switches off the aid's power or pulls the sound delivering portion of the aid—the speaker or the audio guide tube—out of the ear, it will have no effect.

Currently available hearing aids typically have signal processing circuitry designed to adapt to a wearer's audio profile which actually can show significant "dips" indicating impairment in any audio frequency band. Hearing impairment due to age typically involves the higher frequencies that are involved in speech recognition. At the age of 40, the typical person experiences a 20 dB loss of hearing in frequencies above 3 kHz, and by the age of 70, it is a 50 dB loss. For this type of impairment, hearing aids attempt to address these higher frequencies needed to distinguish consonants in spoken speech. They selectively amplify those frequencies while leaving the others either untouched or attenuated in relationship to the other frequencies which are usually associated with ambient noise of little interest. As mentioned, the processing may be tailored to the individual's own hearing loss profile, and it may also be adaptive to different ambient sound environments (such as that of a crowded room, or a concert hall, or a busy street at commute time, for example). However, current approaches are inadequate in addressing situations where the environmental sound is very loud—since it exceeds loudness thresholds, the hearing aid will not amplify the sound, but the wearer could be subjected to further hearing loss. It would be desirable to have hearing aids that could offer some protection against loud sound—especially damaging sound that is sudden and unexpected.

Many hearing aids that seal off the ear canal, e.g. in-the-ear or in-the-canal perform a type of passive noise cancellation by blocking a direct path for sound to enter the ear canal. Some hearing aids have active vent technology which causes a vent in the earpiece of the hearing aid to be open or closed depending on the hearing mode. For example, an open vent allows low frequency sounds to directly enter the ear canal, while a closed vents stops them. When streaming music directly to the hearing aid, closed venting is often preferred because it keeps the low frequency sounds, emanating from the hearing aid, in the ear canal while keeping low frequencies from the outside from mingling, and the sound seems to be more natural to a wearer. In some cases, this vent control operates automatically, in response to detecting the type of sound environment—for example that music is being played. However, up to the present, active vent technology has not been used, or proposed for use, in conjunction with the detection of impulse noise.

The basic idea of active noise cancellation—essentially adding one sound of opposite phase to the phase of the sound to be canceled—dates back at least to the 1930s. Its application to headphones started in the 1950s, but development surged in the late 1980s, and the technology is in widespread use today in many readily available consumer products.

Active noise cancellation (ANC) technology is not built into hearing aids—this is because of the selective amplification and attenuation of certain audio frequencies in relationship to other frequencies order to manage background noise. It is an object of the invention to cancel sudden and very loud sounds that might be damaging to hearing from sudden noises such as a door slamming, someone using a hammer in a home, or someone shouting nearby. However, if someone were intentionally to go to an overly amplified concert, then earplugs or an earmuff would be required.

As noted above, impulsive noise is hazardous to everyone including hearing aid wearers. Moreover, protection from such noise occurring in the environment has not been adequately addressed by hearing aids.

There is therefore a need for devices and methods to detect impulsive sound in the immediate environment of a hearing aid, as a prerequisite to limiting potential harm to the hearing aid wearer. Such devices and methods would preferably be optimized to react automatically and very quickly to prevent those sounds whose waveforms (in terms of volume and volume as a function of time) make them particularly hazardous, from passing beyond the outer ear of the wearer, while interfering as little as possible with "normal" hearing aid operation in the absence of impulsive noise. Ideally, any necessary elements could be added to or even incorporated into hearing aids with minimal if any changes required to the physical housing and operational demands of the devices, so that user comfort and convenience are optimized.

SUMMARY

The present invention includes methods and systems or devices for reducing the volume of potentially harmful impulsive noise that would otherwise enter the ear of a hearing aid wearer, in amplified form, or by passive transmission.

In one embodiment, a hearing aid comprises a microphone and a processing unit. The microphone is configured to receive sound incident on the hearing aid and deliver a corresponding microphone output to the processing unit; and the processing unit is configured to process the microphone output to generate a first processor output, comprising a determination of whether the incident sound comprises potentially harmful impulsive sound, and to generate a second processor output comprising a processed version of the microphone output.

In another embodiment, a method of providing protection to a hearing aid wearer from sudden loud sounds comprises: using a microphone in the hearing aid to receive incident sound and deliver a corresponding microphone output to a processing unit in the hearing aid; and using the processing unit to process the microphone output to generate a first processor output, determined by whether the incident sound comprises potentially harmful impulsive sound, and to generate a second processor output comprising a processed version of the microphone output.

A further understanding of the nature and the advantages of particular embodiments disclosed herein may be realized by reference of the remaining portions of the specification and the attached drawings.

DETAILED DESCRIPTION OF EMBODIMENTS

Described herein are embodiments of devices and methods for protecting a hearing-impaired hearing aid wearer from exposure to dangerously loud noise, by detecting that sound and then using an active noise cancellation (ANC) technique.

Figure 1:
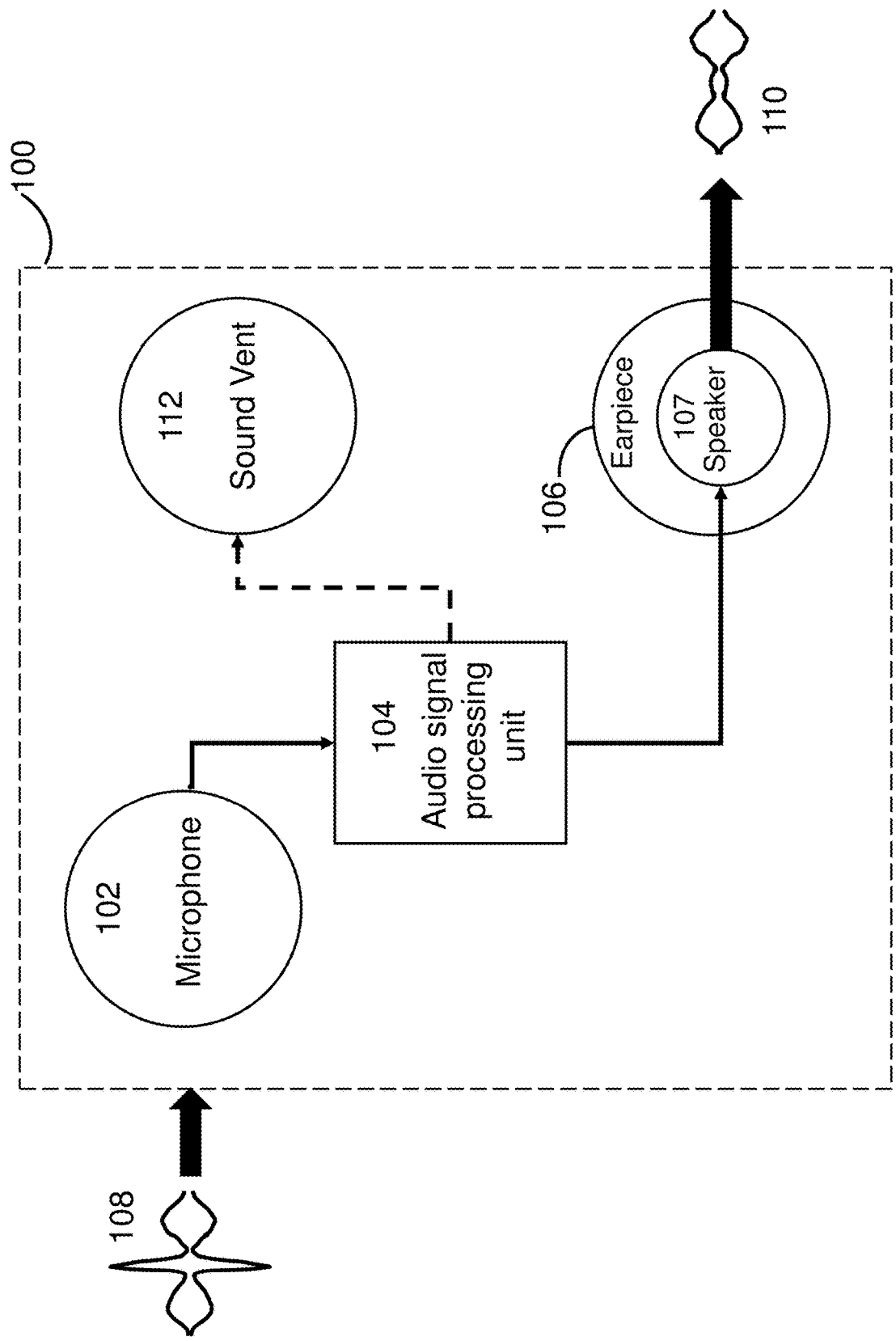
FIG. 1 illustrates a hearing aid according to some embodiments of the present invention.

FIG. 1 illustrates a hearing aid 100 according to some embodiments of the present invention. Hearing aid 100 includes audio signal processing circuitry in processing unit 104 which receives input signals from microphone 102 and delivers output signals to speaker 107 housed in earpiece 106. For the sake of clarity, only a single microphone (102) is shown, but depending on the type of hearing aid, multiple microphones may be present, which may allow the hearing aid to determine the direction from which sound is received. For example, it may determine that a person is speaking directly in front of the wearer and more favorably amplify that sound over the sound coming from the sides of the wearer. For the rest of this disclosure, we will be discussing a single microphone; however, the principles of system operation and related considerations also apply to embodiments with multiple microphones.

Microphone 102, earpiece 106, and speaker 107 are not necessarily any different from microphones and speakers present in hearing aids currently in widespread use, but processing unit 104 includes circuitry configured to address the problems of potentially harmful impulsive noise. To achieve this, it has a sufficiently fine time resolution and a sufficiently high dynamic range to determine when such noise is present, providing a corresponding positive or negative first output. Unit 104 also provides a second output that includes a processed version (typically a frequency dependent amplified version) of the microphone output signal.

In the present invention, one type of response to determining that potentially harmful impulsive sound is present makes use of adjustable (active) sound vents. In some embodiments, hearing aid 100 has at least one active sound vent. For simplicity, just one such vent 112 is shown in the FIG. 1 embodiment. As discussed in the background section, a vent is an opening in the earpiece of the hearing aid that allows direct transmission of environmental sound into the ear, without having undergone electronic signal processing. In some embodiments of the present invention, therefore, if the first output from processing unit 104 indicates that potentially harmful impulsive noise is present, the hearing aid may respond by automatically closing any active sound vents present. Blocking a direct path for any sound passively moving into and through can greatly attenuate the strength of that "passive" sound before it reaches the ear canal.

In the present invention, another type of response to determining that potentially harmful impulsive sound is present makes use of ANC technology. Embodiments that enable this response include ANC circuitry within the hearing aid's processing unit.

Consider hearing aid 100 shown in FIG. 1, receiving sound that is characterized by an exemplary waveform 108, shown in the form of an envelope of amplitude vs time. The upper, positive half of the waveform and the lower, negative half of the waveform would touch in the absence of noise, but in this, more realistic case, there is clearly some low amplitude background noise present. Waveform 108 includes two portions of "true" signal, meaning signal containing sound the hearing aid wearer would want to hear, superimposed on the background noise, and one burst of impulsive noise occurring in a time period between those two signal portions. The ANC circuitry within processing unit 104 operates to deliver a signal to speaker 107 that in turn generates an output sound whose waveform 110 has an envelope substantially free of the central peak, corresponding to the impulsive noise. Throughout this disclosure, the term "substantially free" is used to mean that there is a significant reduction (of at least 50%) in the volume of the corresponding sound. The reduction is ideally 100%, meaning that the noise peak is completely cancelled out, but in practice, a reduction of 50% or more would lead to a significant improvement in terms of potential harm to the hearing aid wearer, who may hear the sound very faintly if at all. The way this reduction may be achieved will be discussed further below.

Figure 2:
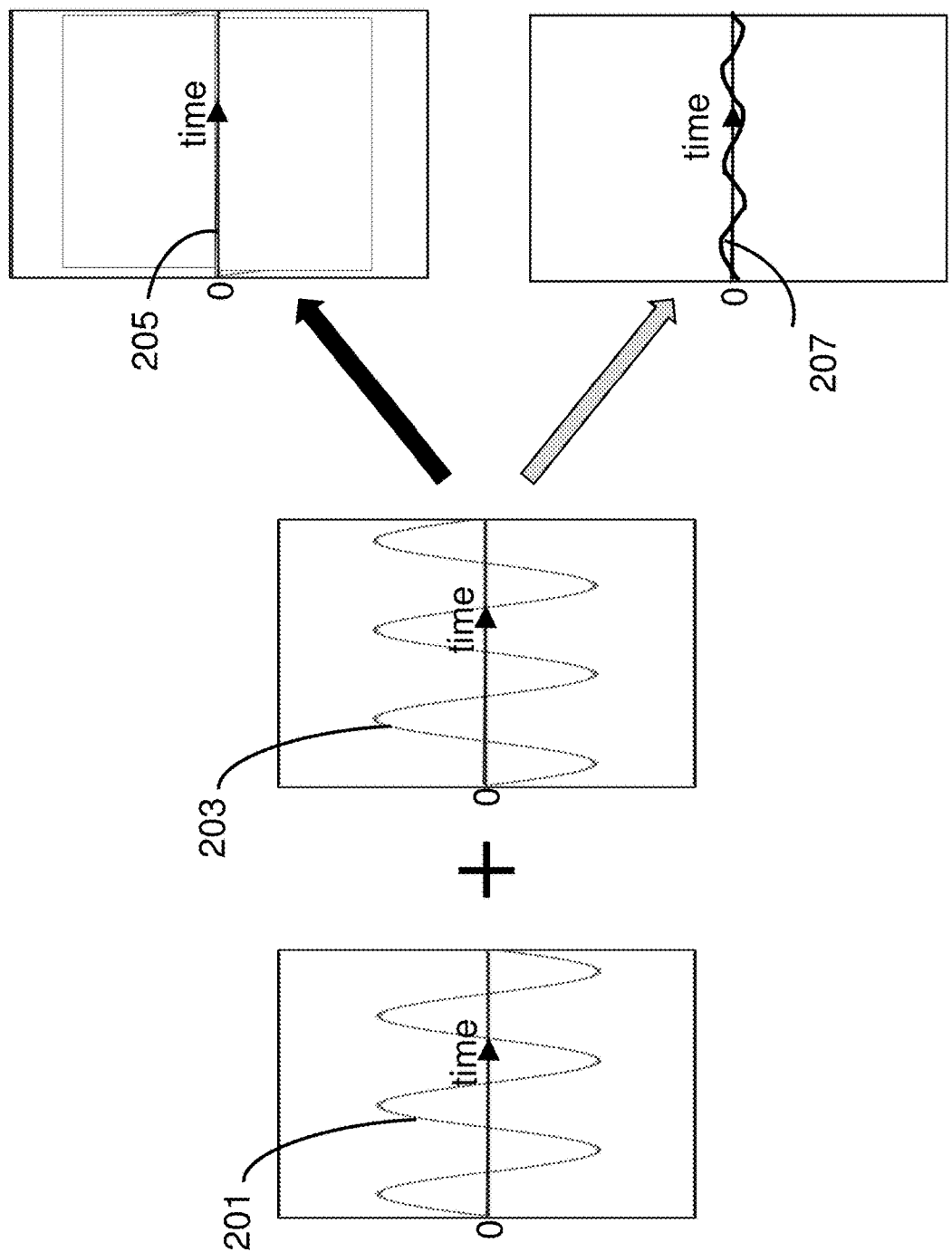
FIG. 2 (Prior Art) illustrates the principles of operation of ANC circuitry.

FIG. 2 shows how prior art ANC circuitry operates to "cancel" either fully or, more realistically, substantially, undesirable sound. Consider for simplicity a hypothetical case, where a microphone receives sound of a pure, single frequency and generates a corresponding electrical waveform 201 characterizing the sound. The ANC circuitry subsequently receiving that electrical waveform responds by generating an "inverse" or "anti-noise" electrical waveform 203, reversed in phase polarity. A combination of the two waveforms is delivered to a speaker, which responds by generating a sound waveform representing that combination, which in the ideal case would be a flat line, unvarying through time, as shown in 205, but which more realistically may be a low amplitude waveform like 207, including a component at the frequency of the input, as noise cancellation may not be perfect.

In audio devices prior to the present invention, active noise cancellation is a feature that the user selects by carrying out a deliberate action, such as pressing a button on a set of headphones, for example. In such devices, all ambient noises external to the headphones are suppressed to some degree.

Prior art implementations have not addressed the particular problems of impulsive noise cancellation. In the present invention, circuitry within the hearing aid processing unit (104 in FIG. 1) is specifically designed to automatically detect and then respond to impulsive noise of particular hazard to hearing aid wearers, operating in conjunction with other, standard hearing aid components, to cancel out such noise (or cause it to be physically blocked) quickly enough to minimize the risk of damage to hearing.

In many embodiments, the circuitry—including the ANC circuitry of course, if present—must be able to handle extremely high noise levels, well over 80 dBA, which is a typical threshold used to distinguish between safe and dangerous loudness levels. Impulsive sounds produced by fireworks or guns, for example, may reach peak loudness values of 140 to 150 dBA. This may impose a high dynamic range requirement on the processing unit electronics.

In many embodiments, the processing unit electronic circuitry must be able to track signals that rise in small fractions of a second, typically 0.5 s or less, from normal, safe loudness levels to dangerously high levels. This imposes correspondingly tight requirements on temporal resolution. Satisfying such requirements allows the objective of automatically protecting the hearing aid wearer, either by electronically cancelling out noise waveforms characteristic of potentially harmful impulsive noise or by mechanically blocking them to be successfully addressed.

In some embodiments, a criterion[1] used by circuitry within the processing unit to determine that noise received is potentially harmful is whether the unit receives a microphone output that corresponds to the microphone detecting a dangerously loud noise level. In other words, if the microphone detects incident sound including a portion characterized by a noise waveform exceeding a loudness threshold deemed to be dangerously high, the processing unit determines that corrective action must be taken, whether that response is to activate ANC circuitry or to close active vents or both. The loudness threshold may be, for example, 120 dBA. In some cases, depending on the environment in which the hearing aid is to be used, other threshold values may be appropriate.

[1] More than one criterion may be used in some embodiments, so it should be understood that in general the determination of potential harm may be based in part or wholly on a criterion such as those discussed in this disclosure In some embodiments, a criterion used by circuitry within the processing unit to determine that noise received is potentially harmful is whether the unit receives a microphone output that corresponds to the microphone detecting impulsive sound that rises from a relatively safe level at such a high rate that it could reach a dangerously high level very quickly, even though it may remain at that high level for a very short time. If the rate of increase is 5 dBA/second, for example, from an initial level of 80 dBA, the combination may warrant the activation of the ANC circuitry. In different circumstances, or for different users, or different hearing aid settings, different combinations of initial level value and rate of increase value may be more appropriate threshold triggers for ANC operation.

In yet other embodiments a criterion used may be a combination of loudness level and rate of increase of loudness, where exceeding thresholds for either one may result in a positive determination of potential harm.

Figure 3:
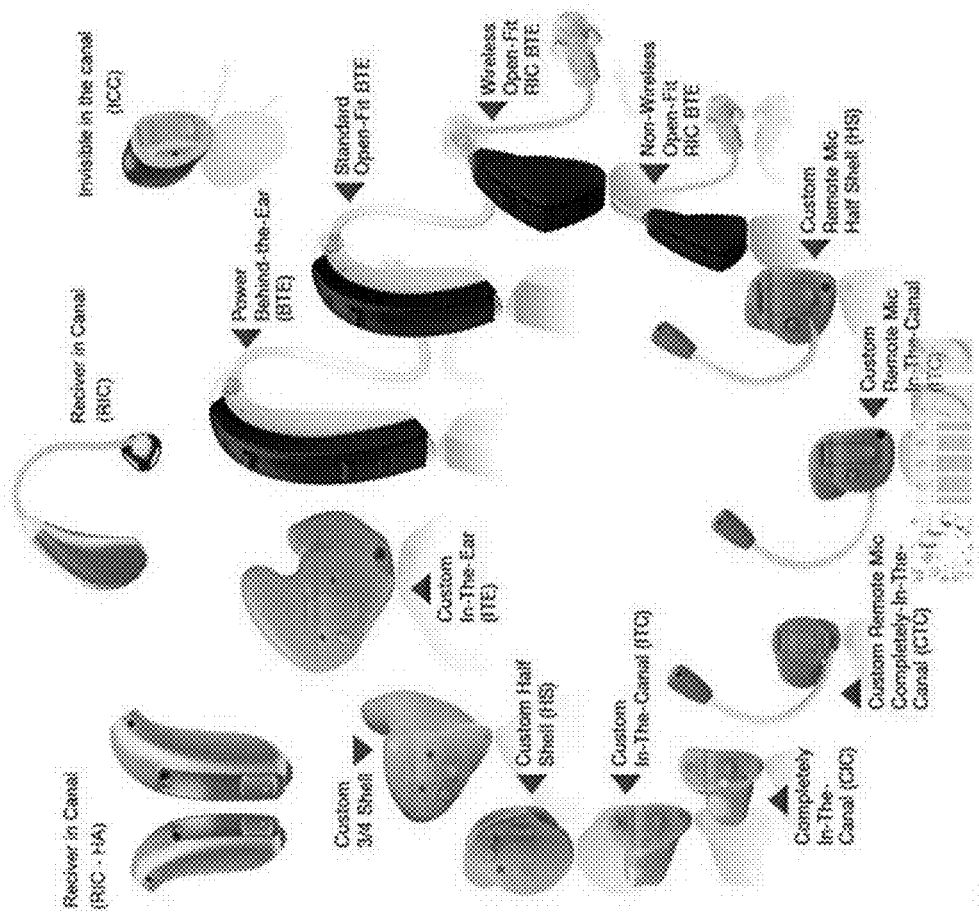
FIG. 3 (Prior Art) shows examples of various configurations of hearing aids.

FIG. 3 shows examples of various configurations of hearing aids in common use. Some keep the microphone, the processing unit, and the speaker within a single housing, the bulk of which lies behind the pinna of the ear, with an audio guide tube hooked over to the front, ready to be positioned within the ear canal. Some others have the portion containing the microphone, the processing unit, and the speaker tucked into a fold of the pinna, again with an audio guide tube leading to the ear canal. Yet others have a microphone and processing unit located in one place, to be hooked behind the ear for example, but the speaker positioned separately either at the entrance to the ear canal, or even within it. The present invention, which essentially depends on the inclusion of ANC circuitry, designed for the impulsive noise cancellation application of interest, in the processing unit, can be implemented in any of these various device configurations.

It should be noted that only certain frequencies of sound may be particularly amplified per the settings of the hearing aid. The other frequencies may be carried at a nominal volume, un-amplified, or attenuated. Depending on the device, some sound may passively pass through the hearing device into the ear canal. While one object of this invention is to attempt to cancel potentially harmful noise that is electronically processed by passage through the hearing aid, another object of this invention is to attempt to cancel potentially harmful noise that would otherwise enter the ear canal passively.

Figure 4:
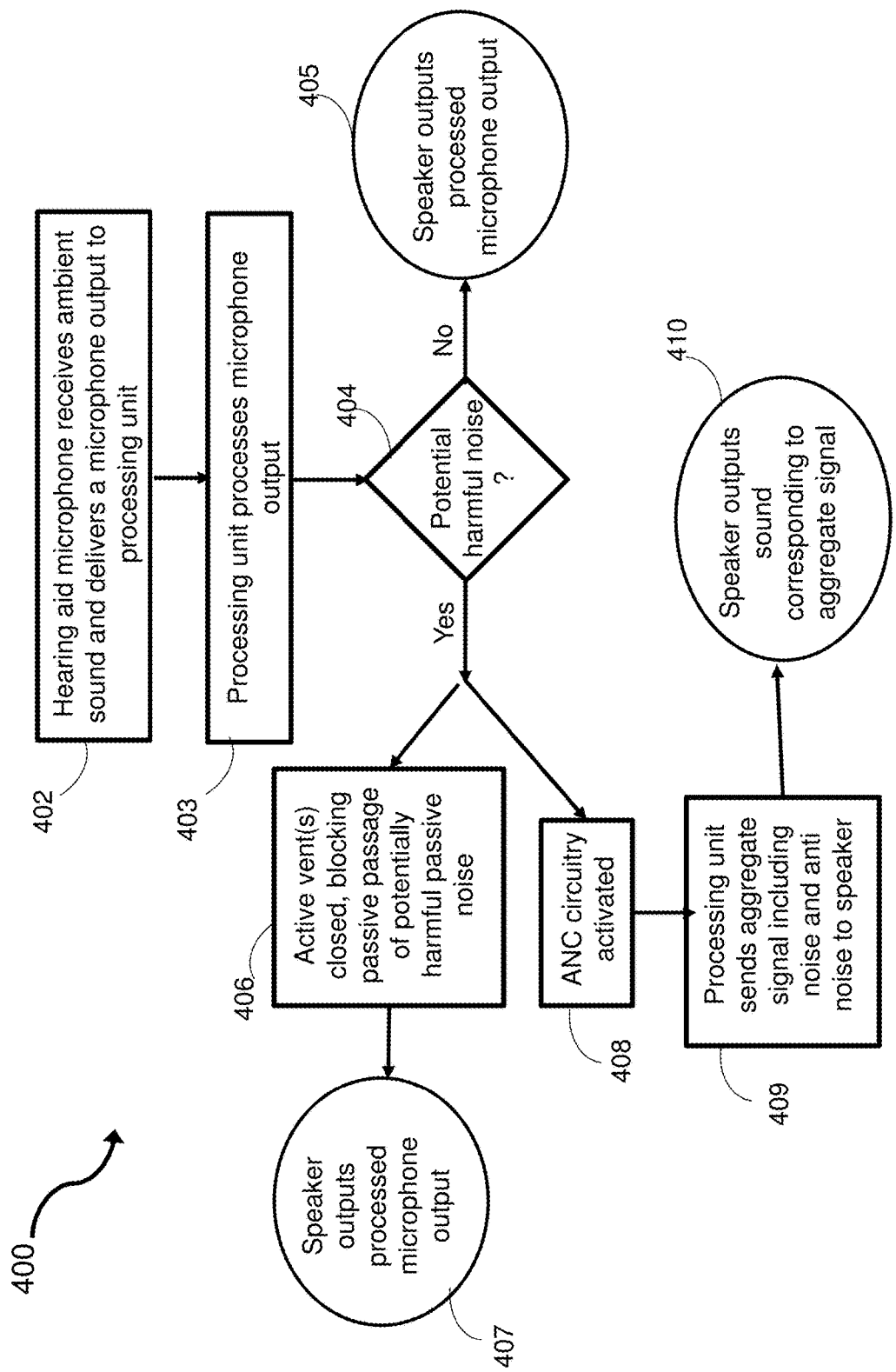
FIG. 4 illustrates a method according to some embodiments of the present invention.

FIG. 4 illustrates a method 400 according to some embodiments of the present invention. At step 402, a microphone in a hearing aid receives ambient sound and delivers its output to a processing unit in the hearing aid. At step 403, the processing unit processes the microphone output. At step 404, the processing unit determines, based on one or more predetermined criteria, whether the sound received by the microphone had included potentially harmful noise. If the result is negative, the processing unit delivers a processed version of the microphone output, typically involving frequency dependent amplification, to a speaker in an earpiece of the hearing aid, so that at step 405, the speaker generates and outputs sound that is free of any harmful noise (as none was present in the ambient sound). If the result of the determination at step 404 is positive, however, at least one of two paths is followed. In certain embodiments, where the hearing aid is equipped with one or more controllable vents, the method proceeds to step 406 where those vents are automatically closed, so that any potentially harmful noise that is passively present in the hearing aid is partially or completely prevented from emerging from the earpiece. Although the figure shows step 407 as occurring after step 406, for simplicity, it should be understood that step 407, where the speaker outputs a processed version of the microphone output, may occur simultaneously or before step 406.

If the path from step 404 to steps 406/407 is the only one followed, which would be the case in the absence of ANC functionality, the speaker output at step 407 would include some potentially harmful sound. In other embodiments, ANC functionality is present, so that the method can advantageously follow the path to steps to 408, 409 and 410 concurrently with the 406/407 path. This "ANC" path will now be described.

At step 408, ANC circuitry is activated, to generate an anti-noise waveform, as discussed above with reference to FIG. 2. Then, at step 409, the processing unit output to the hearing aid speaker is an aggregate, including a processed version of the anti-noise waveform as well as a processed version of the noise waveform, the former hopefully cancelling out or at least substantially reducing the amplitude of the latter. At step 410, the speaker then provides an audible output which is substantially free of sound corresponding to the portion of incident sound characterized by the noise waveform.

In embodiments where there are no active vents present, of course, only the path from 404 to steps 408 through 410 can be followed. In preferred embodiments, active vents and ANC functionality are both present, so noise cancellation and vent closing may be carried out to address the problem of potentially harmful noise more comprehensively.

It should be appreciated that method 400 or variations thereof could be applied to many different types of hearing aids in common use, as shown in FIG. 3 and discussed above. Examples of predetermined criteria that may be applied to determine at step 404 whether the waveform profiles are potentially harmful, and so should trigger either noise cancellation using ANC circuitry or vent closing (or both), have also been discussed above.

Embodiments of the present invention offer a major advantage over prior art in this field, in addressing impulsive noise, and in doing so reliably and conveniently, without depending on any active involvement of the hearing aid wearer. Retrofitting currently available hearing aids to carry out the inventive concepts described herein should be quite feasible.

Although the description has been given with respect to particular embodiments thereof, these particular embodiments are merely illustrative, and not restrictive.

Any suitable programming language can be used to implement the routines of particular embodiments including C, C++, Java, assembly language, etc. Different programming techniques can be employed such as procedural or object oriented. The routines can execute on a single processing device or multiple processors. Although the steps, operations, or computations may be presented in a specific order, this order may be changed in different particular embodiments. In some particular embodiments, multiple steps shown as sequential in this specification can be performed at the same time.

Particular embodiments may be implemented in a computer-readable storage medium for use by or in connection with the instruction execution system, apparatus, system, or device. Particular embodiments can be implemented in the form of control logic in software or hardware or a combination of both. The control logic, when executed by one or more processors, may be operable to perform that which is described in particular embodiments.

Particular embodiments may be implemented by using a programmed general purpose digital computer, by using application specific integrated circuits, programmable logic devices, field programmable gate arrays, optical, chemical, biological, quantum or nanoengineered systems, components and mechanisms may be used. In general, the functions of particular embodiments can be achieved by any means as is known in the art. Distributed, networked systems, components, and/or circuits can be used. Communication, or transfer, of data may be wired, wireless, or by any other means.

It will also be appreciated that one or more of the elements depicted in the drawings/figures can also be implemented in a more separated or integrated manner, or even removed or rendered as inoperable in certain cases, as is useful in accordance with a particular application. It is also within the spirit and scope to implement a program or code that can be stored in a machine-readable medium to permit a computer to perform any of the methods described above.

A "processor" includes any suitable hardware and/or software system, mechanism or component that processes data, signals or other information. A processor can include a system with a general-purpose central processing unit, multiple processing units, dedicated circuitry for achieving functionality, or other systems. Processing need not be limited to a geographic location, or have temporal limitations. For example, a processor can perform its functions in "real time," "offline," in a "batch mode," etc. Portions of processing can be performed at different times and at different locations, by different (or the same) processing systems. Examples of processing systems can include servers, clients, end user devices, routers, switches, networked storage, etc. A computer may be any processor in communication with a memory. The memory may be any suitable processor-readable storage medium, such as random-access memory (RAM), read-only memory (ROM), magnetic or optical disk, or other non-transitory media suitable for storing instructions for execution by the processor.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

Thus, while particular embodiments have been described herein, latitudes of modification, various changes, and substitutions are intended in the foregoing disclosures, and it will be appreciated that in some instances some features of particular embodiments will be employed without a corresponding use of other features without departing from the scope and spirit as set forth. Therefore, many modifications may be made to adapt a particular situation or material to the essential scope and spirit.

We claim:

1. A hearing aid comprising:
a microphone; and
a processing unit;
wherein the microphone is configured to receive sound incident on the hearing aid and deliver a corresponding microphone output to the processing unit; and
wherein the processing unit is configured to process the microphone output to determine whether the incident sound comprises potentially harmful impulsive sound, and to generate a processor output comprising a processed version of the microphone output.

2. The hearing aid of claim 1, wherein the determination is based in part on whether the incident sound received by the microphone comprises a portion characterized by a noise waveform meeting a predetermined criterion.

3. The hearing aid of claim 2, wherein the predetermined criterion comprises exceeding a first threshold loudness level.

4. The hearing aid of claim 3, wherein the first threshold loudness level is 120 dBA.

5. The hearing aid of claim 2, wherein the predetermined criterion comprises exceeding a first threshold rise rate beginning at a loudness level equal to a second threshold loudness level.

6. The hearing aid of claim 5, wherein the first threshold rise rate is 5 dBA per second and the second threshold loudness level is 80 dBA.

7. The hearing aid of claim 2, additionally comprising one or more controllable vents, configured to be closed automatically in response to a determination from the processing unit that the incident sound received by the microphone comprises potentially harmful impulsive sound.

8. The hearing aid of claim 1, wherein the processing unit comprises active noise cancellation (ANC) circuitry, the ANC circuitry being activated automatically in response to a determination that the incident sound received by the microphone comprises potentially harmful impulsive sound, and operable to generate an anti-noise waveform that is included in the processor output.

9. The hearing aid of claim 1, additionally comprising an earpiece comprising a speaker,
wherein a housing containing the microphone and the processing unit is configured to be worn either behind, or tucked into a fold of, a pinna of an ear of a user;
wherein the earpiece is configured to be positioned within or at an entrance of the ear canal of the ear; and
wherein an audible output generated by the speaker is delivered from the earpiece directly into the ear canal of the user.

10. A method of providing protection to a wearer of a hearing aid from sudden loud sounds; the method comprising:
using a microphone in the hearing aid to receive incident sound and deliver a corresponding microphone output to a processing unit in the hearing aid; and
using the processing unit to process the microphone output to generate a first processor output, determined by whether the incident sound comprises potentially harmful impulsive sound, and to generate a second processor output comprising a processed version of the microphone output.

11. The method of claim 10, wherein the determination is based in part on whether the incident sound received by the microphone comprises a portion characterized by a noise waveform meeting a predetermined criterion.

12. The method of claim 11, wherein the predetermined criterion comprises exceeding a first threshold loudness level.

13. The method of claim 12, wherein the first threshold loudness level is 120 dBA.

14. The method of claim 11, wherein the predetermined criterion comprises exceeding a first threshold rise rate beginning at a loudness level equal to a second threshold loudness level.

15. The method of claim 14, wherein the first threshold rise rate is 5 dBA per second and the second threshold loudness level is 80 dBA.

16. The method of claim 10, wherein the processing comprises automatically activating active noise cancellation (ANC) circuitry in the processing unit in response to a determination that the incident sound received by the microphone comprises potentially harmful impulsive sound, the ANC circuitry operating to generate a corresponding anti-noise waveform.

17. The method of claim 16, additionally comprising using a speaker in an earpiece of the hearing aid to generate an audible output corresponding to the second processor output;
wherein the second processor output comprises a combination of a signal corresponding to the noise waveform and a signal corresponding to the anti-noise waveform, such that the audible output generated by the speaker and potentially heard by a wearer of the hearing aid is substantially free of sound corresponding to the portion of incident sound characterized by the noise waveform.

18. The method of claim 17,
wherein a housing containing the microphone and the processing unit is worn either behind, or tucked into a fold of, a pinna of an ear of a user;
wherein the earpiece is positioned within or at an entrance of the ear canal of the ear; and
wherein the audible output generated by the speaker is delivered from the earpiece directly into the ear canal of the user.

19. The method of claim 11, additionally comprising automatically closing one or more controllable vents in response to a determination that the incident sound received by the microphone comprises potentially harmful impulsive sound.

* * * * *